(12) United States Patent
Lenzenhuber et al.

(10) Patent No.: US 11,571,270 B2
(45) Date of Patent: Feb. 7, 2023

(54) PACKAGE FOR A MEDICAL TOOL WITH AUTOMATIC TOOL RECOGNITION, AND PACKING METHOD USING SUCH A PACKAGE

(71) Applicant: Aesculap AG, Tuttlingen (DE)

(72) Inventors: Frederick Lenzenhuber, Tuttlingen (DE); Roland-Alois Högerle, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 78 days.

(21) Appl. No.: 17/271,625

(22) PCT Filed: Sep. 4, 2019

(86) PCT No.: PCT/EP2019/073579
§ 371 (c)(1),
(2) Date: Feb. 26, 2021

(87) PCT Pub. No.: WO2020/049044
PCT Pub. Date: Mar. 12, 2020

(65) Prior Publication Data
US 2021/0315655 A1    Oct. 14, 2021

(30) Foreign Application Priority Data
Sep. 5, 2018  (DE) .............. 10 2018 121 682.3

(51) Int. Cl.
*A61B 50/30* (2016.01)
*A61B 90/98* (2016.01)
*A61F 2/00* (2006.01)

(52) U.S. Cl.
CPC .............. *A61B 50/30* (2016.02); *A61B 90/98* (2016.02); *A61F 2/0095* (2013.01)

(58) Field of Classification Search
CPC ........ A61B 50/30; A61B 90/98; A61F 2/0095
USPC .................................. 206/363, 370
See application file for complete search history.

(56) References Cited

U.S. PATENT DOCUMENTS

| | | | |
|---|---|---|---|
| 8,087,584 B2 * | 1/2012 | Grimard | A61B 90/98 235/487 |
| 9,280,738 B2 * | 3/2016 | Dor | G06K 19/04 |
| 9,498,294 B2 * | 11/2016 | Rigsby | A61B 90/40 |
| 9,592,101 B2 * | 3/2017 | Bovet | G06K 19/07749 |
| 9,721,064 B2 * | 8/2017 | Khajavi | G16H 40/20 |
| 10,368,958 B2 * | 8/2019 | Wehrle | H04B 17/27 |

(Continued)

FOREIGN PATENT DOCUMENTS

| | | |
|---|---|---|
| CN | 108304897 A | 7/2018 |
| DE | 102007016537 A1 | 10/2008 |

(Continued)

OTHER PUBLICATIONS

German Search Report received in Application No. 10 2018 121 682.3 dated May 20, 2019, 12 pages.

(Continued)

*Primary Examiner* — Jacob K Ackun
(74) *Attorney, Agent, or Firm* — Christopher A. Rothe; Culhane Meadows, PLLC

(57) ABSTRACT

A package for a medical tool has a receiving space for the medical tool. The package has a readable data carrier with tool-specific data. The package is usable in a method for automatic identification of a medical tool.

31 Claims, 5 Drawing Sheets

(56) References Cited

U.S. PATENT DOCUMENTS

Figure 1:
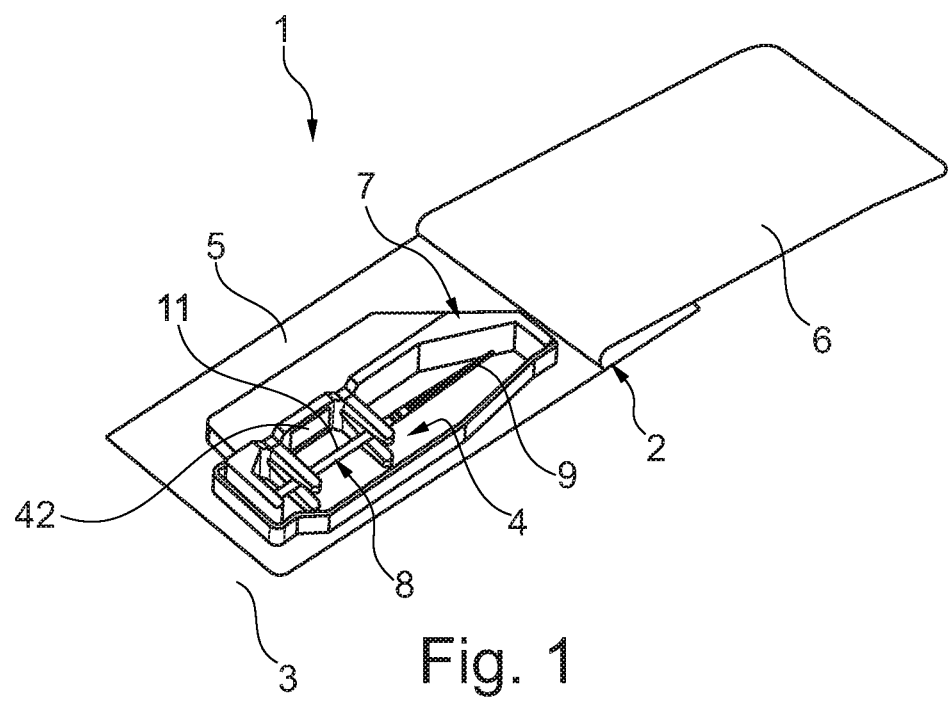

| | | | |
|---|---|---|---|
| 2006/0109105 A1 | 5/2006 | Varner et al. | |
| 2006/0145871 A1* | 7/2006 | Donati | A61B 90/98 340/539.1 |
| 2006/0244593 A1* | 11/2006 | Nycz | A61B 90/98 340/572.1 |
| 2006/0244597 A1* | 11/2006 | Tethrake | A61F 2/4657 340/572.1 |
| 2007/0215507 A1 | 9/2007 | Glenn et al. | |
| 2008/0177267 A1* | 7/2008 | Sands | A61B 90/98 235/492 |
| 2008/0230422 A1* | 9/2008 | Pleil | A61B 90/98 606/280 |
| 2008/0230423 A1* | 9/2008 | Loeffler | A61B 90/90 606/300 |
| 2009/0266889 A1* | 10/2009 | Turner | A61B 90/98 705/28 |
| 2011/0023343 A1* | 2/2011 | Turner | A61B 90/96 40/299.01 |
| 2013/0092564 A1* | 4/2013 | Doherty | A61B 90/90 206/216 |
| 2014/0125482 A1* | 5/2014 | Rigsby | A61L 2/00 340/539.13 |
| 2014/0251845 A1 | 9/2014 | Roesler | |
| 2015/0224247 A1* | 8/2015 | McDorman | B65B 55/10 206/569 |
| 2015/0283332 A1 | 10/2015 | Woehr | |
| 2016/0228188 A1* | 8/2016 | Sweeney | A61B 17/17 |
| 2017/0224859 A1 | 8/2017 | Broninx et al. | |
| 2017/0360523 A1 | 12/2017 | Khajavi et al. | |
| 2018/0153639 A1* | 6/2018 | Wehrle | A61B 50/30 |
| 2022/0096201 A1* | 3/2022 | Lenzenhuber | A61B 90/50 |

FOREIGN PATENT DOCUMENTS

| | | |
|---|---|---|
| DE | 202011050118 U1 | 6/2011 |
| DE | 102013004168 A1 | 9/2014 |
| WO | 2018013413 A1 | 1/2018 |
| WO | 2018052966 A1 | 3/2018 |

OTHER PUBLICATIONS

International Search Report received in Application No. PCT/EP2019/073579 dated Dec. 18, 2019, 17 pages.

International Written Opinion received in Application No. PCT/EP2019/073579 dated Dec. 18, 2019, 16 pages.

Written Opinion received in International Application No. PCT/EP2019/073579 dated Dec. 18, 2019, with translation, 14 pages.

* cited by examiner

PACKAGE FOR A MEDICAL TOOL WITH AUTOMATIC TOOL RECOGNITION, AND PACKING METHOD USING SUCH A PACKAGE

CROSS-REFERENCE TO RELATED APPLICATIONS

This application is the United States national phase entry of International Application No. PCT/EP2019/073579, filed Sep. 4, 2019, and claims the benefit of priority of German Application No. 10 2018 121 682.3, filed Sep. 5, 2018. The contents of International Application No. PCT/EP2019/073579 and German Application No. 10 2018 121 682.3 are incorporated by reference herein in their entireties.

FIELD

The present invention relates to a package, in particular a sterile package, for a medical tool, comprising a receiving space for the medical tool. It furthermore relates to a method for automatically identifying a medical tool by means of a package according to the invention.

BACKGROUND

Various packages and devices for medical products and in particular tools are known. Packages of medical products such as implants and tools with pointed and/or sharp operative portions, for example in the form of cutting or sawing edges, milling heads and drills or thread portions, are subject to special requirements. In addition to protecting users from injury before and in particular after use of the product, it is also necessary to protect the packaged product from undesirable influences such as contamination and damage.

A further requirement for the package is suitable identification of the product packaged in it, which is particularly important if the packaged product is not visible as such (since it is covered by the package, for example) or the product is not recognizable and/or identifiable (for example, since certain identity features such as the material, dimensions or similar features cannot be readily identified for the product). However, reliable and unambiguous identification of a medical product, such as a surgical instrument, a surgical tool or an implant, is of utmost importance in terms of patient safety.

Another important aspect of medical tools can be the transfer and communication of tool-specific information. This can be, for example, information about whether a particular tool is suitable for a particular application and/or what its condition is. For example, in the case of medical tools, it is often essential to know whether and how often it has been used, what its service life is and what its stock levels are. Such information is difficult or impossible to convey and maintain using standard packages.

It is the prior art to identify the packaged tool for the user by means of labels attached to or in the package. The disadvantage here is that the user cannot readily identify with certainty which tool is in the package without a separate and careful inspection of the label and/or the package. Furthermore, in the case of such labels, displaying of additional information, such as the maximum usability, dimensions, materials, etc., may be difficult and require unconditional care on the part of the supplier as well as when the user tries to identify it, for example due to soiling or wear. In addition, the handling in particular of sterile products such as surgical instruments and tools can be subject to restrictions (such as time pressure or stress during an operation) when they are removed from the package, which can make it difficult for the user to record and/or document product-specific data. This is critical in particular because incorrect use of medical tools due to inadequate recording of the respective tool and its properties or use characteristics can quickly lead to serious negative consequences, in particular for a patient. Finally, known packages offer no or only a limited possibility of documented tool recognition.

Packages in which the medical tool is held firmly and/or in a defined position are known from the prior art. An example of such a package is a blister packaging with a clamp in the coupling area of the tool in order to position and hold it in a defined position in the package. Such a package is disclosed, for example, in DE 10 2013 004 168 A1, in which the surgical tool is packaged under sterile conditions in a plastic package, the package is made up of at least two parts and consists of an inner protective packaging for sensitive parts of the surgical tool and a sealable blister packaging that accommodates the protective packaging. Furthermore, a method for packaging sterile surgical tools is proposed in which the surgical tool is packaged in the plastic packaging under sterile conditions, wherein in a first step the surgical tool is first packaged at least partially and in particular with its sensitive cutting edges and working surfaces in the first protective packaging and the protective packaging is transferred together with the surgical tool packaged there into a second blister packaging, where it is secured in position and then sealed with a sealing film. The disadvantage of this packaging is that although the operative edges of the tool are very well protected, the tool itself cannot be identified by the user through the packaging, or only with difficulty.

SUMMARY

Against this background, the present invention is based on the object of reducing the aforementioned disadvantages of the prior art, in particular to provide a package for a medical tool or respectively a tool support provided for arrangement in the package, with which recognition of the respective packaged tool is possible simply and reliably and the risk of incorrect application of the tool can be minimized.

This object is solved according to the present invention by a package/support, i.e. a package, in particular a sterile package, for a medical tool, with a receiving space for the medical tool, wherein the package or the support in the package comprises a readable data carrier with tool-specific data. The preceding object is furthermore solved by a method for automatically identifying a medical tool by means of a package or a support arranged therein according to the invention comprising the following steps:
  inserting the tool into the receiving space of the package by the provider,
  writing tool-specific data on the data carrier by the provider,
  closing of the package by the provider,
  opening of the package by the user,
  identifying the tool by reading the data carrier by the user.

A tool in the sense of the invention is in particular understood to be an operation tool/surgical tool with a generally distal, sharp-edged operative portion for performing an operative function and a proximal coupling portion for coupling the tool with a handle unit, in particular a drive handle unit. Examples of such tools are, in particular, rotating tools as well as sawing tools, including drills, milling cutters, saws, screw adapters, cutting blades or sanding adapters, which are coupled to a handle and/or drive unit in a generally known manner. Furthermore, a tool in the sense of the invention is understood to be a spray nozzle, an HF syringe, an ultrasonic blade, etc. Finally, the term 'tool' in the sense of the invention also includes implants of any type and shape, such as bone and joint implants or partial implants, stents, etc.

It is a particular advantage of the invention that the tool can be automatically recognized when it is removed from the package by the user. The data carrier is designed for preferably wireless communication with external reading and/or writing units. It is particularly advantageous if a handle piece to be used with the tool has a read-out device by means of which the data contained on the data carrier can be recognized and/or read out, since the tool can then be automatically identified when it is connected/arranged/plugged into the handle piece. Data acquired in this way can be transmitted/displayed to the user on a display unit communicating with the handle piece.

The data written on the data carrier may be, in the sense of the invention, an article number, a lot number, a batch number, a best-before date, an expiration date or maximum use date, material, dimensions and geometries, intended use, previous uses and duration of use, inventory levels, etc.

The general idea underlying the invention includes that tool recognition takes place and is passed on to peripheral devices by data transmission and that selected data is displayed to the end customer. At the same time, further data can be logged and processed.

A configuration example of the invention is characterized in that the package comprises an outer packaging. Additionally, it may comprise a holding device/tool support arranged in the receiving space. Such a holding device may advantageously be arranged and/or held in a positionally determined manner in the receiving space. It serves in particular to hold the tool, in particular to hold it in a positionally determined manner and to position it in the receiving space in such a way that contact of sharp operative portions with the package material is avoided and that sharp operative portions are spaced from the package. By providing such a holding device, contact of the tool with parts of the package can be prevented or at least safely minimized, so that abrasion of package material by the tool can be prevented. The holding device and/or the outer packaging may consist at least partially, preferably entirely, of an absorbable material. The receiving space can be formed to be closed by the outer packaging, in particular in a hermetically sealed manner. It can also be formed to be sterile. A particular advantage of the invention is that the data carrier can be read out without having to open the package and giving up sterility.

According to a configuration example of the invention, the holding device is formed separately from the outer packaging. Therefore, the tool held in the holding device can be removed together with the holding device from the outer packaging and can in particular remain in the holding device after unpacking until it is finally used. Preferably, the package and the holding device are designed in such a way that removal can take place by handling the holding device and without direct contacting of the tool, so that the probability of contamination of the tool can be easily and safely minimized, or even avoided altogether. Moreover, the tool can be placed together with the holding device on an instrument table without having to put it down loosely. During a surgery or treatment, the holder can be used in a particularly advantageous manner for intermediate storage of the tool, resulting in better organization and clarity. In addition to the package in the actual sense, the invention can thus provide an independent holder by means of the separate holding device, which, in addition to safe and stable storage of tools during transport in the respective outer packaging, also enables defined positioning and safe handling of the tool during processing (e.g. sterilization) and during preparation of the product during treatment in the operating room. For this purpose, the holding device can be removed from the outer packaging together with the tool held in it and set up.

According to a configuration example of the invention, the data carrier can be an RFID tag or an NFC tag. It is particularly advantageous that its data can be read, written and processed without contact and automatically, in particular at any time, without requiring any special interaction of the user. In particular, the data carrier can be permanently readable. In particular, it can be arranged on the outer packaging or on the holding device. A data carrier can also be arranged both on the outer packaging and on the holding device. The data carrier can in particular be glued on.

According to a configuration example of the invention, the data carrier and the outer packaging or respectively the data carrier and the holding device are firmly or non-detachably connected to each other. Preferably, the data carrier is bonded, molded or pressed thereto. As a result, accidental loosening of the data carrier and unintentional separation of the data carrier and the package/tool are ruled out, so that it can be guaranteed with a high degree of certainty that the data on the data carrier really belongs to the tool located in the package/holding device. This increases patient safety in an advantageous manner.

According to a further configuration example of the invention, the data carrier can be activated. In particular, the data carrier can be activated by relative positioning of the tool relative to the package or outer packaging or holding device. For example, such a relative positioning may close/activate an aerial circuit and/or electrical circuit and/or switching circuit connected to the data carrier, thereby activating the data carrier and allowing it to be read out. This can be caused by the fact that, when the tool is positioned in the package in the intended manner, the electrical circuit and/or aerial circuit and/or switching circuit is open so that it is inactive, for example since the tool itself is insulating and interrupts the circuit, or since the tool deforms the package/outer packaging/holding device in such a way that the circuit is interrupted. According to the method, the data carrier is activated by relative positioning of the product in the receptacle or in the holding device or by removal therefrom for reading out of the data contained on the data carrier or sending of the data contained on the data carrier.

The aerial circuit and/or electrical circuit can be part of the package. In particular, it can be integrated into or arranged or formed on the outer packaging and/or on the holding device. Preferably, the circuit is designed in such a way that it is open, i.e. deactivated, when the tool is arranged in the package in the intended manner, and while the circuit is closed, i.e. activated, when the tool is removed from its intended position. This has the advantage that the data carrier is not read out until the tool is removed from the package, so that unnecessary data traffic and energy consumption can be avoided or reduced. With regard to the method according to the invention, the data carrier can be read out by a reading device preferably located in a handpiece when the tool located in the package, in particular the tool located in the holding device, is inserted into the handpiece intended to receive the tool.

According to the method, the tool can be inserted into the receiving space or be arranged in the holding device and data can be written to the data carrier before or after insertion of the tool into the receiving space or arrangement of the tool in the holding device, preferably under sterile conditions. This allows great flexibility. A configuration example of the method according to the invention provides that a γ sterilization is performed after sealing the package. In this way, sterility can be effected without compromising the safe function of the data carrier. According to a configuration example, writing data on the data carrier can also be performed after the sterilization has been carried out.

It is of particular advantage if, according to a further configuration example of the invention, data read out from the data carrier is displayed to a user of the tool. Alternatively or additionally, data of the tool read out from the data carrier can be stored and/or forwarded to the provider of the tool. The aforementioned processes preferably run automatically, so that the data in particular can be automatically displayed and/or forwarded and/or stored in a database.

The holding device can comprise a base plate. In particular, this can be designed in such a way that it forms a footprint for position-stable placement of the holding device with a tool held therein, in particular in a state unpacked from the package, and/or an abutment structure for abutment against the package. In addition to the footprint, the holding device may have further abutment structures or portions that interact with and abut on the package so as to ensure clear and stable orientation positioning in the receptacle of the package. If the data carrier is integrated into or arranged on such a holding device within the scope of the invention, identification of the tool placed in the holding device, for example on an instrumentation table, is particularly easy within the scope of a medical intervention.

According to a configuration example of the invention, the holding device can have at least two holding structures spaced apart from each other for orientation-determined positioning of the tool. Preferably, each of these is arranged on the base plate and may extend therefrom into the receiving space. In addition to the function of holding the tool, the holding structures can form attachments with which the holding device rests against the package, preferably in such a way that its orientation is secured or fixed in the receptacle of the package. One of the holding structures can be arranged at the end side of the holding device, in particular at the base plate. Another one of the holding structures can be arranged substantially centrally on the holding device, in particular on the base plate. This enables particularly stable holding of the tool in the holding device.

Preferably, one of the holding structures is designed to position the tool in an orientation-determined manner relative to the holding device in a first direction. The other one of the holding structures can be designed to position the tool in an orientation-determined manner relative to the holding device in a second direction and a third direction, wherein the first, second and third directions are orthogonal to each other. By means of such guiding the tool is held stably in the holding device on the one hand, and on the other hand it can be arranged in the holding device and removed from the holding device particularly easily by a user. It is particularly advantageous if, according to a further configuration example of the package, at least one of the holding structures forms a form fit and/or a force fit with the tool, in particular with a coupling structure of the tool.

At least one of the holding structures, in particular both holding structures, can have two holding arms opposite each other. A slit is formed between each of these to receive and hold the tool. The holding arms can be arranged essentially perpendicular to the base plate of the holding device. In a particularly advantageous manner, they can be designed as clamping arms and in particular have resilient properties in a direction transverse to the slit. Removal and arrangement of the tool in the holding structures is particularly easy if, according to one form of the invention, the slit widens in the direction from proximal of the base to distal of the base. This favors largely risk-free handling of both unused and used instruments, so that in particular injury-free disposal of tools in the holding structure is improved and the risk of infection which exists in principle is reduced. According to a further developed embodiment of the invention, the sides of the holding arms facing the slit may be provided with indentations. Such indentations can advantageously form locking pockets for the tool inserted in the slit, so that the tool is held securely in the holding structures and yet can be easily removed by a user.

A particularly user-friendly configuration example of the invention, which avoids injuries of a user by the tool held in the holding device, provides that the holding device comprises a protective lug which protrudes from the base plate into the receiving space and covers a distal end of the tool or a sharp-edged structure of the tool without contact. In this way, a user is protected from injury from any sharp edges of the tool when handling the holding device with the tool held therein.

According to a configuration example of the invention, the package is formed as a blister. Such blisters are inexpensive and can be manufactured for almost any shape of the product and/or holding device. Preferably, the blister packaging may have a lower shell with a recess forming the receiving space for the tool. Such a lower shell can simply be formed with a stability and shape sufficient for the orientation-stable positioning of the holding device and tool. By means of a lid foil arranged on the lower shell in a known manner, the receiving space can be closed in the desired manner, in particular hermetically and/or in a sterile manner. The data carrier can be positioned on the lower shell or on the lid foil.

According to a further configuration example of the invention, the package may comprise a carrier element, for example in the form of a sieve basket. It can be arranged in the package together with the holding device and the tool held thereon, in particular with a plurality of holding devices with the respective tool held thereon. By means of such a carrier element, several holding devices with tools held therein can be handled particularly easily and simultaneously, for example, they can be sterilized and/or placed on an instrumentation table.

According to a further configuration example of the invention, the holding device can be coded, for example by having a colored design. In this way, the invention can in an especially simple way provide a system with which not only different products can be coded in a way that can be easily distinguished by a user, but also such coding or marking of certain tools can be retained even after the tool has been unpacked from the package and assigned to the respective tool. In particular, tools that have already been unpacked and are ready for use on an instrumentation table or in a sterilization facility can be identified particularly easily and reliably by the user. Different tools and/or holding devices can preferably be identified by means of different colors of the holding devices, for example with regard to their indication or to specific product groups, etc. In this way, incorrect combinations can be avoided. In this way, incorrect combinations of tools can be avoided by the coloring of the holding device, which is designed in particular as a plastic injection-molded part, in and outside the package.

According to a further configuration example of the invention, the holding device may be formed as a molded plastic part. If, according to a further developed embodiment of the invention, it is formed as a multi-component injection molding, it can, for example, be provided with a particularly good anti-slip footprint. This enables a stable arrangement of the holding device on an instrument table and/or on a carrier element such as a sieve basket during a processing operation. In addition, this can greatly facilitate the handling of the holding device when removing the unused tool as well as when inserting a used tool. In particular, the data carrier can be molded/injected into the holding device.

It is a particular advantage of the invention that a user in the course of using a particular medical tool can safely, easily, quickly and in particular automatically obtain information about which tool he is currently using or intends to use and/or is/will be placed on a handle unit without having to look at a label or the outer packaging. In particular, a user can automatically and easily recognize whether the product used is suitable or unsuitable for a particular application. A further advantage of the invention is that a user can easily see without having to take inventory which stocks of the tool in question are still in his warehouse (possibly a consignment warehouse).

The present invention offers essential advantages not only for the user but also for the supplier of packaged medical devices and tools: the invention enables him to determine particularly easily which products/tools have been combined and/or used. Furthermore, he can trace overloading of tools and any associated product damage. Finally, the invention makes it possible for a supplier to offer customized logistics to a customer.

In summary, it can be said that the invention enables recognition, in particular automatic recognition, of the respective product used, in particular of the respective tool inserted on a handle or drive unit. Furthermore, the invention enables a particularly simple and largely error-proof maintenance and/or transmission of any product-related data written on the data carrier. The invention enables in particular the following advantages:
- direct, automated product identification for both a user and a provider (supply chain management (SCM), service, error analysis)
- transmission of any number of additional data to the user and/or the provider (supply chain management (SCM), service, failure analysis)
- for the user, the invention creates a way to automatically record product-related data in a patient record in a timely manner.

In other words, the present invention provides a tool reception or tool support adapted and provided to be received in or formed in a sterile package in order to form a component of the package. The tool support has at least one, preferably several, (axially) spaced shaft-receiving clamps (each consisting of two spring-elastic or spring-elastically mounted clamping arms/clamping jaws) which is/are arranged on a base or base plate, preferably in one piece of material, and preferably each forms at least one or several bulging sections for (partially) surrounding reception of a tool shaft.

In order to prevent axial movement of the tool/tool shaft in the tool reception clamp(s), two (axially) spaced end stops are provided/mountable on the base plate.

The readable data carrier (tag) can be placed in particular on/in the base plate axially between the two end stops and preferably axially between two shaft support clamps.

BRIEF DESCRIPTION OF THE DRAWING FIGURES

Figure 2:
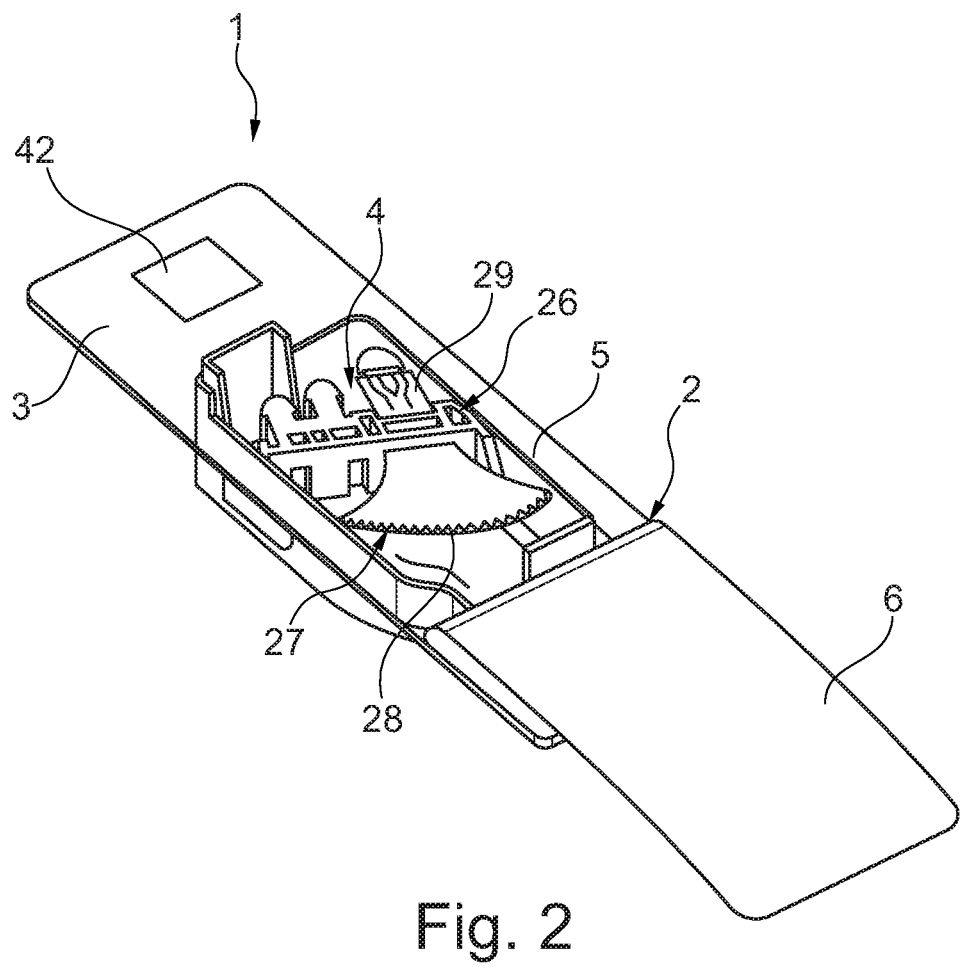
Figure 3:
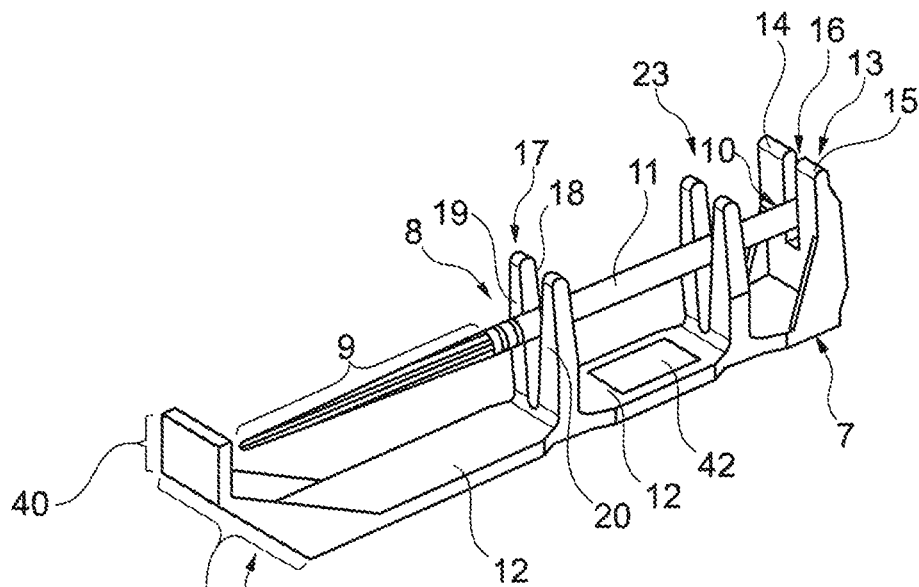
Figure 4:
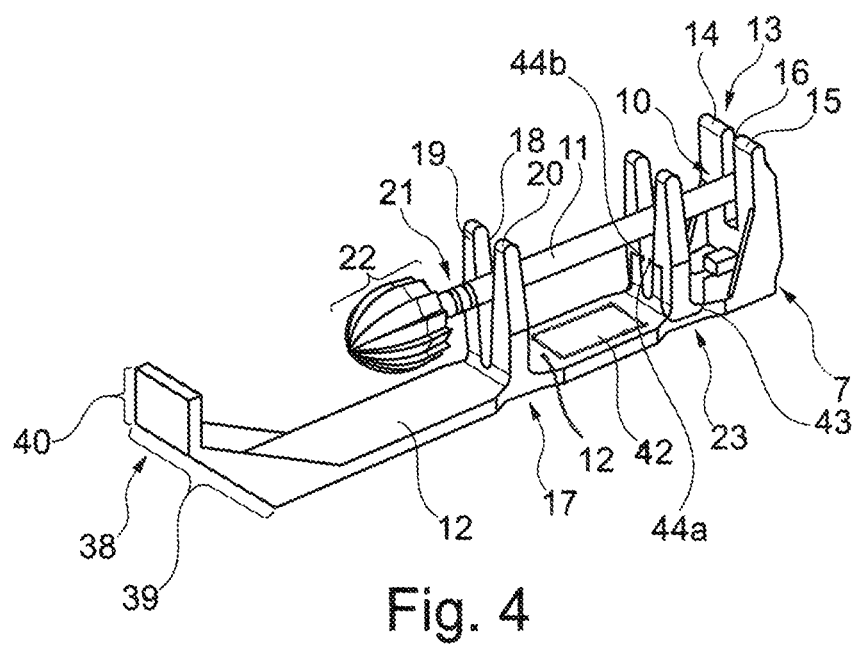
Figure 5:
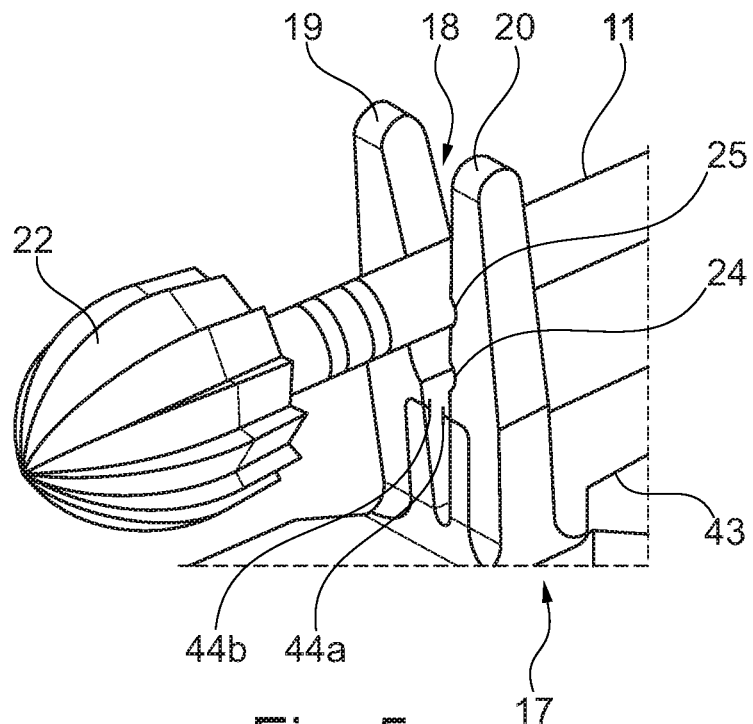
Figure 6:
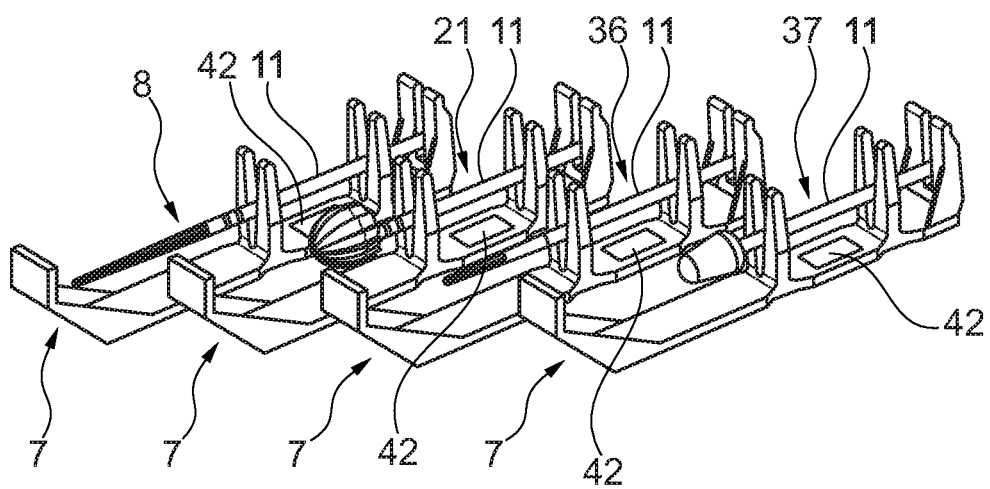
Figure 7:
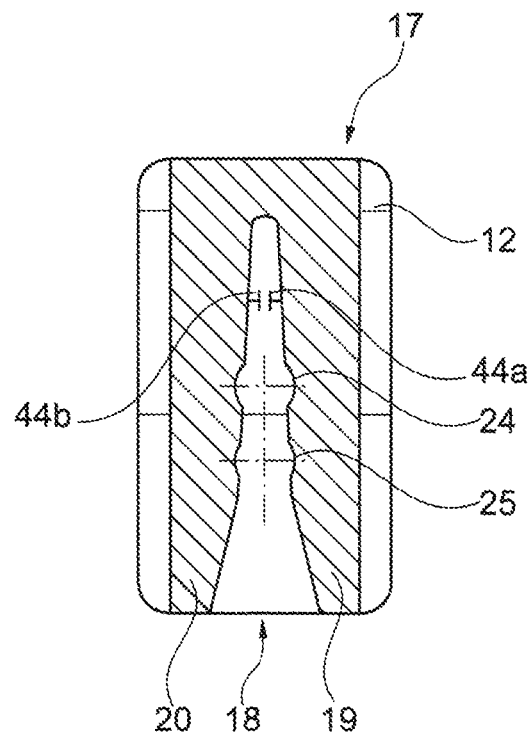
Figure 8:
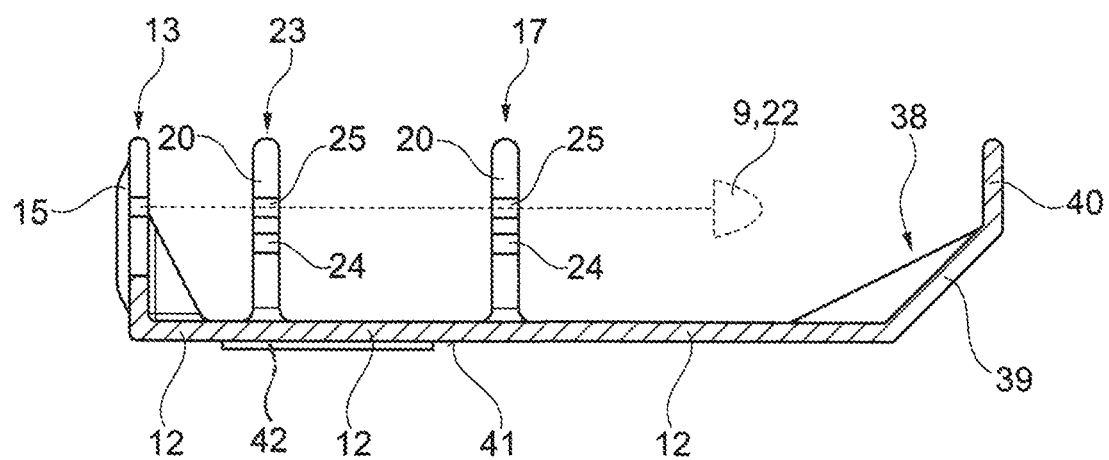
Figure 9:
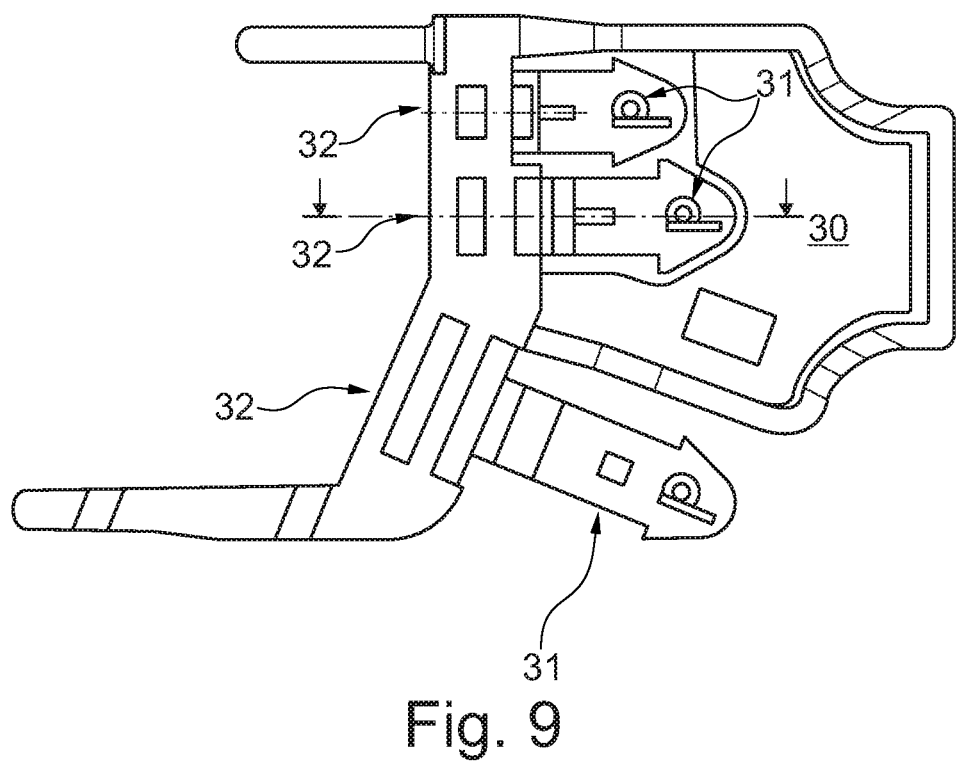
Figure 10:
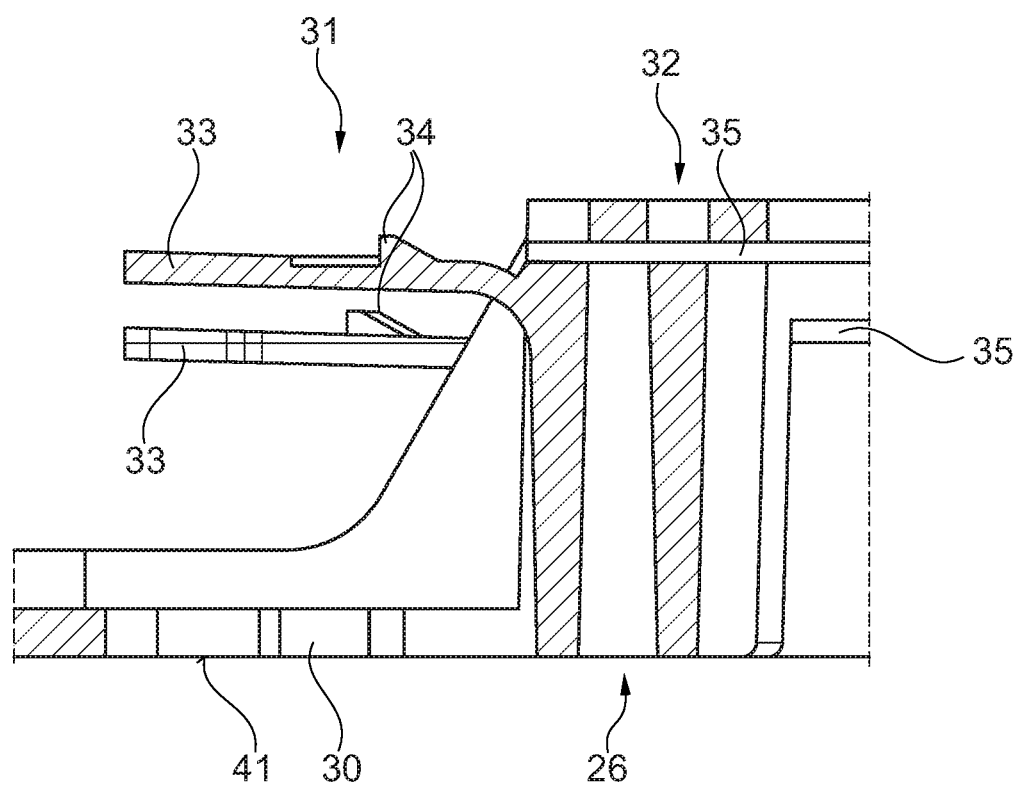

Further features and advantages of the present invention will be apparent from the following exemplary and non-limiting description of the invention by means of figures. These are merely schematic in nature and serve only for understanding the invention. They show:

FIG. 1 shows a perspective view of a configuration example of a package according to the invention, FIG. 2 shows a perspective view of a configuration example of a package according to the invention, FIG. 3 shows a perspective view of a holding device with a tool held therein, FIG. 4 shows a perspective view of a holding device with a tool held therein, FIG. 5 shows an enlarged detail of FIG. 4, FIG. 6 shows a plurality of holding devices, each with a tool held therein, FIG. 7 shows a sectional view of a holding device through its holding structure transverse to the longitudinal axis, FIG. 8 shows a sectional view of a holding device in the direction of the longitudinal axis, FIG. 9 shows a top view of the holding device of FIG. 2, and FIG. 10 shows a sectional view of the holding device of FIG. 9.

DETAILED DESCRIPTION

FIGS. 1 and 2 each show a configuration example of a package 1 according to the invention. This comprises an outer packaging 2 in the form of a blister 2 with a lower shell 3 with a recess 4 formed therein and an edge 5 surrounding the recess 4. The outer packaging 2 also comprises a lid foil 6 arranged on the surrounding edge 5 of the lower shell 3 and hermetically sealing the recess 4, said lid foil 6 being shown in FIGS. 1 and 3 respectively in a partially opened state. Both the lower shell 3 and the lid foil 6 can be made of an absorbable material.

In the recess 4 of the outer packaging 2 of FIG. 1, a holding device 7 with a tool 8 held therein is arranged as an example of a packaged product (see also FIG. 3). The tool 8 in the present embodiment is a drill 8, at the distal end of which an operative portion 9 in the form of a drill head 9 is formed and at the proximal end of which a coupling structure 10 is formed for arranging the tool 8 in a tool reception (not shown) of a drive handle unit. The tool 8 has an elongated tool shaft 11 between the operative portion 9 and the coupling structure 10.

According to the invention, a data carrier 42, here in the form of a radio readable/recordable data carrier, for example in the form of an NFC tag or RFID tag 42, is arranged on the holding device 7 of the configuration example shown in FIG. 1. In the configuration example of FIG. 2, a data carrier 42, again in the form of an RFID tag 42, is arranged on the outer packaging 2. Data specific to the respective tool 8 is stored on the data carriers 42 of FIGS. 1 and 2.

The holding device 7 of the configuration example of FIG. 1 is shown in FIG. 3 without the outer packaging 2. It is designed as a plastic molded part, consists entirely of a resorbable material and has a base plate 12. A first holding structure 13 is formed at the proximal end of the base plate 12. This holding structure 13 comprises two holding arms 14, 15, which are parallel to each other, extend from the base plate 12 essentially orthogonally in the direction of the tool 8 and which are connected to the base plate 12. A slit 16 is formed between the holding arms 14, 15 as a receptacle for the coupling structure 10 of the tool 8. A second holding structure 17 is formed centrally of the base plate 12, which extends from the base plate 12 in the same direction as the first holding structure 13. The second holding structure 17 also has two holding arms 19, 20 which are opposite each other and form a receiving slit 18 between them, and which are both arranged essentially orthogonally to the base plate 12. A third holding structure 23 is formed between the first holding structure 13 and the second holding structure 17, which is essentially similar to the second holding structure 17 and which is therefore not described further. The data carrier 42 is arranged on the side of the base plate 12 facing the tool 8, in this case glued on.

FIG. 4 shows a holding device 7 similar to the holding device 7 of FIG. 3 with another tool 21, here in the form of a milling adapter 21, and another data carrier 42 in the form of a radio readable/recordable data carrier, for example in the form of an NFC tag or NFC tag 42. Like the drill 8 of FIGS. 1 and 3, the milling adapter 21 has a coupling structure 10 and a tool shaft 11 and differs from the drill 8 in that its distal operative portion 22 is formed as a milling head 22. Nevertheless, the invention allows the drill 8 and the milling head 21 to be accommodated in the same holding devices 7. The data carrier 42 is again arranged on the base plate 12, close to the coupling structure 10 of the milling adapter 21. It is connected to an aerial circuit 43. This circuit has two contacts 44*a* and 44*b*, which are electrically separated from each other when the tool 21 is arranged in the holding device 7 as intended in FIG. 4, so that the aerial circuit 43 is interrupted. According to another configuration example, the aerial circuit can be located on the lower side of the holding device 7 and can be quite large. The indicated circuit closure is to symbolize that the function of the aerial is then activated there. Likewise, the circuit closure can be accomplished by other constructive designs, for example by leaf springs, etc. The basic idea, however, is that a circuit is always closed or opened when the tool is removed.

In the configuration example shown in FIG. 4, the two contacts 44*a* and 44*b* are provided in the area of the third holding structure 23. However, it is also conceivable that the contacts 44*a* and 44*b* are provided in different areas of the holding device 7. For example, the contact 44*a* can be provided/arranged in the area of/at the third holding structure 23 and the contact 44*b* can be provided/arranged in the area of/at the first holding structure 13. If the tool 21 is arranged in the holding device 7, the aerial circuit 43 is preferably also interrupted/open in this case. If the contacts 44*a* and 44*b* are provided in different areas of the holding device 7, unintentional contacting without the tool can be avoided more effectively.

FIG. 5 shows the second holding structure 17 of the holding device 7 in an enlarged detailed view. The side surfaces of the holding arms 19, 20 facing each other are each provided with two indentations 24, 25 of different sizes arranged one above the other, each for receiving tool shafts 11 of different diameters (see also FIG. 7, which shows the second holding structure 17 in a sectional view transverse to the longitudinal axis of the tool 8, 21). The holding arms 19, 20 have certain elastic spring properties and can perform a spring movement relative to each other, so that the slit 18 can widen when a tool 8, 21 is inserted and the holding arms 19, 20 spring back to their original position as soon as the shaft 11 of the corresponding tool 8, 21 is arranged in the indentation 24, 25. In this way, the tool 8, 21 is held securely in the holding device 7. In particular, it can be held clamped between the holding arms 19, 20. When the tool 8, 21 is in the indentation, however, the holding arms 19, 20 do not spring back completely to their original position, but are still spaced apart from each other by a certain amount, so that the two contacts 44*a*, 44*b* of the aerial circuit 43 electrically connected to the data carrier are separated from each other and the aerial circuit 43 is interrupted. Only when the tool 8, 21 is removed from the slit 18 located between the two holding arms 19, 20 can the holding arms 19, 20 spring back completely into their original position, in which the two contacts 44*a*, 44*b* are in contact with each other, so that when the tool 8, 21 is removed the aerial circuit 43 is closed and the data carrier 42 electrically connected to it can be read out.

A protective lug 38 is arranged at the end (operative-portion side) of the base plate 12 opposite the first holding structure 13. The protective lug 38 projects from the base plate 12 first with an inclined portion 39 at an oblique angle (here of about 45°) and is then bent by a further angle to an end portion 40, so that its end facing away from the base plate 12 is arranged approximately transversely to the latter. As in particular FIG. 8 shows, the protective lug 38 projects from the base plate 12 to such an extent that the respective distal end of the operative portion 9, 22 is covered without contact. This design of the protective lug 38 creates a good grip possibility in the form of the inclined portion 39 for being grasped by a user, for example from the position shown in FIG. 6 from an instrumentation table, wherein the operative portion is covered so that its contacting by the user can be safely prevented and thus a risk of injury can be minimized. FIG. 8 also shows a radio readable/recordable data carrier, for example in the form of an NFC tag or RFID tag 42, affixed to the lower side of the base plate 12.

FIG. 6 shows that the holding device 7 is suitable for receiving and holding different tools 8, 21 as long as they have a substantially similar basic shape with a shaft 11 and a coupling structure 10 at the proximal end and actually differ only with respect to their respective operative portion 9, 22. Exemplarily shown in FIG. 6 are the drill adapter 8, the milling adapter 21, a screwing adapter 36 and a grinding adapter 37, wherein the shaft diameters of the adapters 36, 37 are smaller than those of the adapters 8, 21, so that the adapters 36, 37 are arranged in the indentation 24 with smaller diameter and the adapters 8, 21 are arranged in the indentation 25 with larger diameter. Furthermore, it can be seen from FIG. 6 as well as from FIG. 3 that the holding device 7 (the same applies to the holding device 26 described below), in addition to fixing the position of the tool 8, 21 in the packaged state, i.e. in the state shown in FIGS. 1 and 2, can be used as a holding device which can be used separately from the outer packaging 2, in order to set down the tool, for example when it is provided in the course of an operation or during sterilization. The lower side 41 of the base plate 12, 30 forms a footprint 41 for this purpose, on which the holding device 7, 26 with a tool held therein can be placed in a stable manner. Finally, FIG. 7 shows that the two contacts 44*a* and 44*b* of the aerial circuit 43 are in contact with each other when there is no tool 8, 21 in the holding device 7. FIG. 5 shows a spacing and would connect when the tool is removed.

A holding device 26 with a tool 27 held therein is arranged in the recess 4 of the outer packaging 2 of FIG. 2. The tool 27 is in the present embodiment a sawing adapter 27, at the distal end of which an operative portion 28 in the form of a saw blade and at the proximal end of which a coupling structure 29 are formed for arranging the tool 27 in a tool reception (not shown) of a drive handle unit.

As shown in FIGS. 9 and 10, the holding device 26 comprises a base plate 30, on the upper side of which a radio readable/recordable data carrier, for example in the form of an NFC tag or RFID tag 42 is attached as a data carrier with tool-specific data. Also arranged on the base plate 30 are a first holding structure 31 and a second holding structure 32, which are spaced apart from the base plate 30 in a direction transverse to the latter. The holding device 26 of FIGS. 9 and 10 is provided with a total of three first and three second holding structures 31, 32 in order to be able to accommodate sawing adapters of different shapes and/or sizes. The three different holding structures 31, 32 are basically similar in design, so that only one of each will be described below.

The first holding structure 31 has a spring arm 33 which can perform a spring movement in the direction towards the base plate 30. On its side facing away from the base plate 30, the spring arm 33 is provided with a latching structure 34, here in the form of a snap-in nose 34, which can interact with the coupling structure 29 of the sawing adapter 27 and can thus fix the latter in position relative to the second holding structure 32 and in a direction parallel to the base plate 30. The second holding structure 32 is formed as a slit 35 through which the coupling structure of the sawing adapter 27 can be pushed until it engages with the first holding structure 31 and the nose 34. The slit 35 is dimensioned such that the sawing adapter 27 is positioned in an orientation transverse to the base plate 30 and in the remaining direction parallel thereto. The slit 35 and the spring arm 33 are designed and positioned relative to each other in such a way that the sawing adapter 27 can only be brought into its intended position, in which it is latched with the snap-in nose 34, by springing in the spring arm 33.

In order to remove the sawing adapter 27, the spring arm 33 is to be manually deformed by an operator in the direction of the base plate 30 in such a way that the coupling structure of the sawing adapter 27 can be released from the snap-in nose 34 and the sawing adapter 27 can be pulled out of the slit 35 in a direction parallel to the base plate 30. A used sawing adapter 27 can be particularly easily arranged again in the holding device 26 for intermediate storage and/or disposal by simply pushing it again in the direction of the snap-in nose 34 through the slit 35, wherein the spring arm 33 deflects until the snap-in nose 34 engages with the coupling structure 29 of the sawing adapter 27 and the latter is secured in position in the holding device 26.

Activation of the data carrier 42 can be realized in the configuration example shown in FIGS. 9 and 10 as follows: each second holding structure 32 formed as a receiving pocket may be designed/formed as a button. For example, each receiving pocket comprises applied conductive traces or stranded wires. The sawing adapter 27 is configured/designed to close a circuit. This can preferably be realized in that the sawing adapter 27 is made of a conductive material, in particular metal, or at least has conductive layers such as a deposited metal (in the case in which the sawing adapter 27 is made, for example, of ceramic, plastic or composite material). For example, upon removal of the sawing adapter 27 from the holding device 26, the circuit through the sawing adapter 27 may be (momentarily) closed and the data carrier 42 may be activated.

The invention claimed is:

1. A package comprising:
   an outer packaging being a blister packaging having a lower shell with a recess forming a receiving space and a lid foil arranged on the lower shell and closing the receiving space;
   a holding device arranged in the receiving space and having a holding structure;
   a medical tool held by the holding structure of the holding device; and
   a readable data carrier with medical tool-specific data, the readable data carrier fixedly connected to the holding device.

2. The package according to claim 1, wherein the holding device is arranged in the receiving space in a position-determined manner, and/or the medical tool is held in a position-determined manner in the holding device.

3. The package according to claim 1, wherein the readable data carrier is an RFID tag or an NFC tag.

4. The package according to claim 1, wherein the readable data carrier and the holding device are glued, cast or pressed together.

5. The package according to claim 1, wherein the readable data carrier is configured to be activated by relative positioning of the medical tool in the package or respectively the outer packaging or respectively the holding device.

6. The package according to claim 1, wherein the package comprises an electric circuit and/or aerial circuit connected to the readable data carrier.

7. A method for automatically identifying a medical tool by a package according to claim 1, the method comprising the following steps:
   inserting the medical tool into the receiving space of the package;
   writing the medical tool-specific data on the readable data carrier;
   closing the package;
   opening the package; and
   identifying the medical tool by reading out the readable data carrier only after opening the package.

8. The method according to claim 7, wherein the medical tool is inserted into the receiving space or is arranged in the holding device and the medical tool-specific data is written on the readable data carrier before or after introducing the medical tool into the receiving space or arranging the medical tool in the holding device.

9. The method according to claim 7, wherein a γ sterilization is carried out after closing the package.

10. The method according to claim 7, wherein the readable data carrier is read out by a reading device when the medical tool is inserted into a handpiece for receiving the medical tool.

11. The method according to claim 7, wherein the medical tool-specific data read out from the readable data carrier is displayed to a user of the medical tool and/or the medical tool-specific data of the medical tool read out from the readable data carrier is stored and/or forwarded to the provider of the medical tool.

12. The method according to claim 7, wherein the readable data carrier is activated for reading of the medical tool-specific data located on the readable data carrier or sending of the medical tool-specific data located on the readable data carrier by:
   relative positioning of the medical tool in the receiving space or respectively in the holding device; or
   removal of the medical tool from the package.

13. The package according to claim 1, further comprising an aerial circuit and/or electric circuit connected to the readable data carrier, wherein the aerial circuit and/or electric circuit is activated by relative positioning of the medical tool in the package such that when the medical tool is held by the holding structure of the holding device, the aerial circuit and/or electric circuit is open and deactivated, and when the medical tool is removed from the holding structure of the holding device, the aerial circuit and/or electric circuit is closed and activated, such that the readable data carrier is read out when removing the medical tool from the holding structure of the holding device.

14. The package according to claim 13, wherein the aerial circuit and/or electric circuit comprises two electrical contacts that are electrically separated when the medical tool is arranged in the holding device, the two electrical contacts being electrically connected when the medical tool is removed from the holding device.

15. The package according to claim 1, wherein the holding device comprises a base plate, and the holding structure is formed as two parallel holding arms connected to the base plate and extending from the base plate orthogonally, with a slit formed between the two parallel holding arms, the medical tool being receivable in the slit.

16. The package according to claim 1, wherein the holding device comprises a base plate, and the holding structure is formed as a spring arm having a latching structure, the spring arm extending parallel to the base plate and deflectable in a spring movement in a direction towards the base plate.

17. A package comprising:
a receiving space;
a medical tool;
a holding device arranged in the receiving space and having a holding structure which is configured to hold the medical tool;
a readable data carrier with medical tool-specific data; and
an aerial circuit and/or electric circuit connected to the readable data carrier; wherein
the aerial circuit and/or electric circuit is activated by relative positioning of the medical tool in the package such that when the medical tool is held by the holding structure of the holding device, the aerial circuit and/or electric circuit is open and deactivated, and when the medical tool is removed from the holding structure of the holding device, the aerial circuit and/or electric circuit is closed and activated, such that the readable data carrier is read out when removing the medical tool from the holding structure of the holding device.

18. The package according to claim 17, wherein the aerial circuit and/or electric circuit comprises two electrical contacts that are electrically separated when the medical tool is arranged in the holding device and that are electrically connected when the medical tool is removed from the holding device.

19. The package according to claim 17, the package further comprising an outer packaging being a blister packaging having a lower shell with a recess forming the receiving space and a lid foil arranged on the lower shell and closing the receiving space.

20. A package comprising:
a medical tool;
a clamp configured to securely hold the medical tool;
a readable data carrier configured to store tool-specific data about the medical tool; and
a circuit integrated into the clamp and connected to the readable data carrier,
the circuit being switchable between a closed state, in which the data carrier reads out the tool-specific data, and an open state,
the medical tool being mountable in the clamp in a secured state,
the medical tool further being movable relative to the holding device from the secured state to a released state,
the circuit being switchable from the open state to the closed state in response to the medical tool being moved to at least one of the secured state and the released state.

21. The package according to claim 20, wherein the circuit is switched to the closed state in response to the medical tool being moved from the secured state to the released state.

22. The package according to claim 20, wherein the circuit is switched to the closed state in response to the medical tool being removed from the clamp.

23. The package according to claim 20, wherein the circuit is switched to the closed state in response to the medical tool being mounted in the clamp.

24. The package according to claim 20, wherein the circuit comprises a first contact integrated in a first section of the clamp and a second contact integrated in a second section of the clamp.

25. The package according to claim 24, wherein the clamp comprises a slit between the first section of the clamp and the second section of the clamp, the medical tool configured to be inserted into the slit to secure the medical tool in the clamp in the second state.

26. The package according to claim 25, wherein the first section of the clamp and the second section of the clamp are movable relative to one another between a first state, in which the slit has a first width, and a second state, in which the slit has a second width greater than the first width.

27. The package according to claim 26, wherein the first contact is in contact with the second contact when the first section of the clamp and the second section of the clamp are in the first state, and the first contact is physically separated from the second contact when the first section of the clamp and the second section of the clamp are in the second state.

28. The package according to claim 27, wherein the first section of the clamp and the second section of the clamp move to the second state in response to the medical tool being inserted into the slit.

29. The package according to claim 28, wherein the clamp is formed of spring-elastic material, such that the first section of the clamp and the second section of the clamp spring back to the first state when the medical tool is removed from the slit.

30. The package according to claim 29, wherein the medical tool comprises an insulating material configured to be positioned between the first contact and the second contact when the medical tool is inserted into the slit,
wherein mounting of the medical tool in the clamp switches the circuit to the open state, and
wherein removal of the medical tool from the clamp switches the circuit to the closed state such that the data carrier reads out the tool-specific data.

31. The package according to claim 27, wherein the medical tool comprises a conductive material configured to be positioned between the first contact and the second contact when the medical tool is inserted into the slit,
wherein insertion of the medical tool in the clamp switches the circuit to the closed state and the data carrier reads out the tool-specific data.

* * * * *